US012329568B2

(12) United States Patent
Lee

(10) Patent No.: US 12,329,568 B2
(45) Date of Patent: Jun. 17, 2025

(54) SYSTEMS AND METHODS FOR MONITORING ABLATION PROGRESS USING LINEAR EBUS DATA

(71) Applicant: Veran Medical Technologies, Inc., St. Louis, MO (US)

(72) Inventor: Christopher Lee, St. Louis, MO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 219 days.

(21) Appl. No.: 18/200,161

(22) Filed: May 22, 2023

(65) Prior Publication Data

US 2024/0389970 A1  Nov. 28, 2024

(51) Int. Cl.
| | |
|---|---|
| A61B 8/08 | (2006.01) |
| A61B 8/12 | (2006.01) |
| A61B 18/02 | (2006.01) |
| A61B 34/20 | (2016.01) |
| A61B 90/00 | (2016.01) |
| A61B 18/00 | (2006.01) |

(52) U.S. Cl.
CPC .............. *A61B 8/0841* (2013.01); *A61B 8/12* (2013.01); *A61B 18/02* (2013.01); *A61B 34/20* (2016.02); *A61B 90/36* (2016.02); *A61B 2018/00541* (2013.01); *A61B 2018/00577* (2013.01); *A61B 2018/0293* (2013.01); *A61B 2090/378* (2016.02)

(58) Field of Classification Search
CPC .. A61B 2018/0293; A61B 8/0841; A61B 8/12
See application file for complete search history.

(56) References Cited

U.S. PATENT DOCUMENTS

| | | | |
|---|---|---|---|
| 2017/0020558 A1* | 1/2017 | Xu .......................... | A61B 8/483 |
| 2021/0052314 A1* | 2/2021 | Holsing ............. | A61B 18/1492 |
| 2023/0075251 A1* | 3/2023 | Romo ................ | A61B 1/00148 |

FOREIGN PATENT DOCUMENTS

| | | |
|---|---|---|
| WO | 2021034744 | 2/2021 |
| WO | 2024243177 | 11/2024 |

OTHER PUBLICATIONS

"International Application Serial No. PCT US2024 030313, International Search Report mailed Sep. 20, 2024", 4 pgs.

(Continued)

*Primary Examiner* — Colin T. Sakamoto
(74) *Attorney, Agent, or Firm* — Schwegman Lundberg & Woessner, P.A.

(57) ABSTRACT

A system and method are presented for treating targeted tissue using cryoablation. A linear endobronchial ultrasound (EBUS) device is positioned adjacent the targeted tissue and is used to guide a percutaneously inserted cryoprobe into the targeted tissue. The EBUS device is partially rotated in order to create multiple image slices that are combined together. To overcome the acoustic shadow created by the ice ball, a 3D model is created of the ice ball based on the locations identified on visible portion of the ice ball's peripheral surface. These locations are mirrored across an axis defined for the cryoprobe to define an approximate location for the hidden, non-visible periphery. This model is then displayed along with the location of the targeted tissue and an indication of the killing zone of the ice ball defined by a selected isotherm.

27 Claims, 12 Drawing Sheets

(56) References Cited

OTHER PUBLICATIONS

"International Application Serial No. PCT US2024 030313, Written Opinion mailed Sep. 20, 2024", 7 pgs.

Golkar, Ehsan, "GPU-based 3D iceball modeling for fast cryoablation simulation and planning", International Journal of Computer Assisted Radiology and Surgery, Springer, DE, vol. 14, No. 9, (Aug. 12, 2019), 12 pgs.

Rewcastle, John C, "A model for the time dependent three-dimensional thermal distribution within iceballs surrounding multiple cryoprobes", Medical Physics, AIP, Melville, NY, US, vol. 28, No. 6, (Jun. 1, 2001), 13 pgs.

* cited by examiner

SYSTEMS AND METHODS FOR MONITORING ABLATION PROGRESS USING LINEAR EBUS DATA

TECHNICAL FIELD

The present disclosure relates to linear endobronchial ultrasound (linear EBUS), in which an ultrasound probe is inserted into the lungs in order to monitor a cryoablation procedure on targeted tissue.

BACKGROUND

Cryosurgery or cryoablation is a procedure in which abnormal or target tissue is destroyed through a freezing process. The freezing of tissue cells causes the cells or organelles within the cells to rupture. The cryosurgery process typically involves the insertion of a device (a "cryoprobe") into the abnormal tissue and then cooling the device. In most circumstances, the cooling of the cryoprobe is accomplished by passing a high-pressure gas, such as argon, through the device. The cooling of the cryoprobe in this manner creates an "ice ball" of frozen tissue that is approximately centered on the distal end of the cryoprobe.

It is important that the size, shape, and location of the ice ball be accurately determined in order for the procedure to be successful. If the ice ball is larger than necessary, healthy tissue surrounding the target tissue will be unnecessarily damaged. If the ice ball is too small, abnormal tissue that was to be killed through the process will survive.

SUMMARY

One embodiment of the present disclosure presents a method for treating a tumor or other targeted tissue using cryoablation. The method begins by identifying the location of the targeted tissue, such as by performing pre-procedure CT imaging. The images created can be combined into 3D images, or into a 3D model of the patient or of an organ of the patient. This 3D model of the patient's anatomy (e.g., lung) is then registered to the patient's physical anatomy such as, for example, by using an electromagnetic field and location sensor (or other surgical navigation technology).

During the procedure, a linear endobronchial ultrasound (EBUS) device is positioned in the trachea-bronchial tree of the patient adjacent the targeted tissue. The EBUS will then image the targeted tissue, and at this point the ultrasound image data can be used to fine tune the registration between the 3D model of the patient's anatomy and the patient's physical or real anatomy. The EBUS images may also be used to guide a cryoprobe that is inserted percutaneously into the targeted tissue. For example, similar to the linear EBUS device, the cryoprobe may have electromagnetic sensors that allow for a determination of the location and orientation of the tip of the probe within the electromagnetic field. The cryoprobe then begins freezing the targeted tissue.

At this time, the EBUS device is partially rotated in order to create multiple image slices that are combined together to create 3D image and model of the targeted tissue and the developing ice ball. Because of the impedance mismatch that results from the nature of the ice ball relative to the surrounding unfrozen tissues, the ultrasound energy that is emitted from the EBUS device may be unable to pass beyond the peripheral surface (or perimeter) of the ice ball. To allow the practitioner the ability to understand the relationship of the growing ice ball and the targeted tissue, a 3D model is created of the ice ball. This model starts by identifying the visible portion of the ice ball's peripheral surface and identifying the location of those points. These locations are then compared with the axis defined by the orientation of the cryoprobe's tip. A line segment perpendicular to the axis is identified to the point on the peripheral surface. An opposite line segment of the same length is then used to identify a point that represents an approximation of the hidden, non-visible side of the ice ball. Sufficient points are "mirrored" across the cryoprobe axis in order to define an approximate location for a large segment of the hidden, non-visible periphery. This is then combined with the points on the visible surface to create a model of the ice ball.

The created model is presented on a computerized user interface (typically on a computer display) to the practitioner, with the interface also showing the location of the targeted tissue in the same 3D space. Furthermore, the interface will present an approximate isotherm line/surface within the interior of the ice ball model. This isotherm shows the approximate reach of the killing zone of the ice ball. In one embodiment, this isotherm line is drawn at the estimated extent of a sustained −40° C. temperature. The system is designed to recognize when the ice ball being formed is the first or second ice ball at this location. If it is the second ice ball, the isotherm line/surface may be drawn at the approximate location of a higher temperature, as an effective kill is possible at a higher temperature (e.g., −30° C.) if the tissue has been subject to repetitive freeze-thaw cycles. The periphery and isotherm line are redrawn in real-time as the EBUS device detects the expanding periphery of the ice ball. The practitioner can then change their planned freezing process as a result of the display shown on user interface 1200.

DETAILED DESCRIPTION

Ice Ball Formation

Cryoablation is typically performed to kill abnormal tissue that has been discovered in a patient prior. In most cases, the exact location of the abnormal tissue is identified through imaging using traditional technologies such as CT or MRI imaging. This data can then be used to create a 3D model of the patient including the abnormal tissue. An analysis of that 3D model can lead to the development of a treatment plan that includes targeting the abnormal tissue for ablation. In some circumstance, this analysis determines that cryoablation should be used to ablate the targeted tissue.

Figure 1:
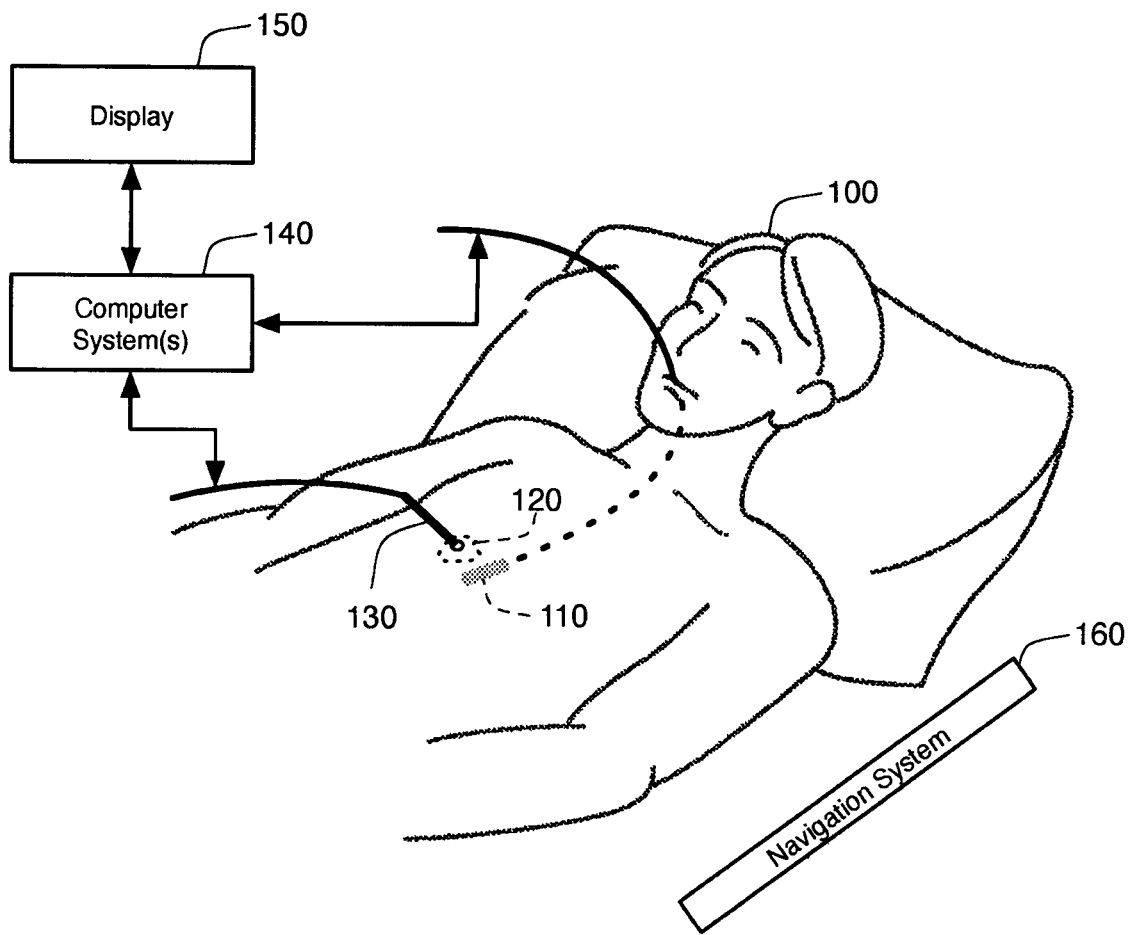
FIG. 1 is a perspective view of the percutaneous insertion of a cryoprobe under the guidance of endobronchial ultrasound (EBUS) device.

In this context, a patient 100 is be prepared for treating a patient through using a cryoablation procedure, as shown in FIG. 1. A computer system 140 is in communication with equipment used on the patient, and is responsible for the presentation of the 3D model of the patient on display 150. The patient 100 is registered with a navigation system 160 using an initial registration process, which is well known in the prior art. In some instances, this registration process involves placing the patient 100 in an electromagnetic field created by navigation system 160, directing a navigated surgical instrument in 3D space monitored by the navigation system 160 to a known location of the patient's physical anatomy (e.g., a main carina), and then updating reference coordinate system data to co-locate the 3D model to the patient's physical anatomy. Devices having electromagnetic (EM) sensors can detect this field and also be located within the field, meaning that the devices in the 3D space can also be located with respect to the 3D model of the body. EM field-based surgical navigation techniques are but one of many known surgical navigation techniques which can be deployed in various embodiments of the present disclosure. In these embodiments, the EM field generator in the navigation system 160 would be replaced with a different navigation technology device that allows for navigated position of instruments registered with the 3D model of the patient.

Figure 2:
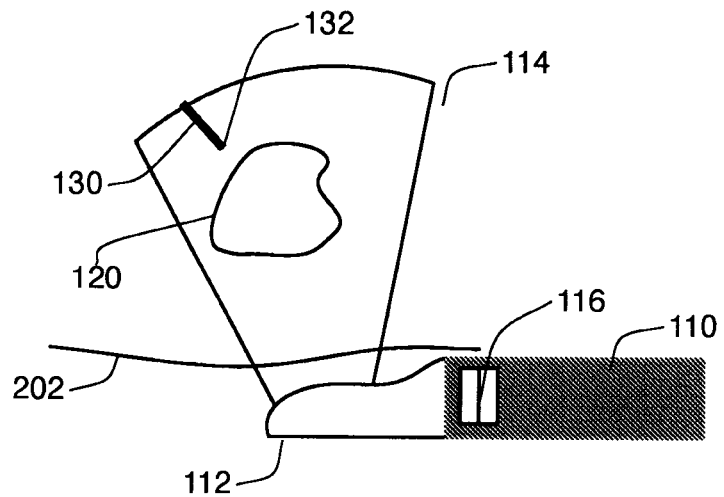
FIG. 2 is a side schematic illustration of the ultrasound transceivers of an EBUS device defining a view region showing targeted tissue.

As shown in FIG. 1, when the procedure is ready to begin, the targeted tissue 120 in the patient 100 is located using a linear endobronchial ultrasound (EBUS) device 110. In one embodiment, the linear EBUS device 110 has a curvilinear array of ultrasound transducers 112 at its distal tip, as is shown in FIG. 2. The EBUS device 110 can even form part of a bronchoscope, such as the Olympus BF-UC180F available from Olympus (Tokyo, JP).

The EBUS device 110 is passed into the tracheobronchial tree and steered to a location proximate to the targeted tissue 120. The ultrasound transducers 112 are acoustically coupled to the airway wall 202 either by direct contact or by expanding a saline filled balloon that surrounds the transducers 112 and contacts the airway wall 202 (the balloon is not shown in FIG. 2). Once so acoustically coupled, the ultrasound transducers 112 can collect an image of the tissue on the other side of the airway wall 202. The image area is shown in FIG. 2 as image area 114. In this case, the image area 114 shows a portion of the targeted tissue 120.

The EBUS device 110 incorporates EM sensors 116, located proximal to the ultrasound transducers 112, that sense the electromagnetic field that is present around the patient 100. It is important that these EM sensors 116 can determine all six degrees of freedom (DoF), which comprise the x, y, and z positions as well as pitch, roll, and yaw. Typically, a physical sensor can sense five of the six DoFs. Techniques such as that shown in U.S. Pat. No. 8,696,549 (owned by Veran Medical Technologies, Inc. of St. Louis, MO) can be used to determine the sixth DoF from a sensor 116 that senses only five. Alternatively, two offset five DoF sensors can determine the six degrees of freedom. Once the x, y, z position of the tip is known, along with its pitch, yaw, and roll orientation, the computer systems 140 can interpret the ultrasound image data acquired by the sensors 116 and developed a strong understanding as to the location this image data.

In one embodiment, the imaging data from the image area 114 can be used to identify the exact location of the targeted tissue 120 with respect to the EBUS device 110. Because the location of the targeted tissue 120 is also known with precision within the 3D model of the patient, and the EBUS device 110 can also be located with respect to this 3D model. As a result, this new information can be used to fine-tune the registration process between the model and the patient. In other words, the imaging data from image area 114 may show that minor corrections are needed to exactly register the location information created by the electromagnetic fields and EM sensors 116 with the 3D model.

After this registration fine-tuning, the ultrasound transducers 112 are then used to monitor the percutaneous insertion of a cryoprobe 130 into a patient 100. The tip 132 of the cryoprobe 130 may be specially designed to improve identifiability under ultrasound, such as by applying grooves or other physical aberrations which are highly visible to the ultrasound energy (e.g., echogenic features). As shown in FIG. 2, the ultrasound imaging of the EBUS device 110 can view this tip 132 and help the practitioner direct the cryoprobe 130 to the targeted tissue 120.

FIG. 1 also shows one or more computer systems 140 that send the signals and power to the EBUS device 110 and the cryoprobe 130, receive signals from those devices 110, 130, analyze those signals, and then display the results of that analysis to the user. Such computer systems 140 are standard computing devices that comprise CPUs, short-term and long-term memory storage, computer programming, display systems, and interfaces as necessary to communicate with and control devices 110, 130. Computer systems 140 are also responsible for performing the calculation and presentation steps in the methods described herein. The computer systems 140 can comprising a single computer or multiple computers acting separately or in concert to control the devices 110, 130 and perform the described methods.

Figure 3:
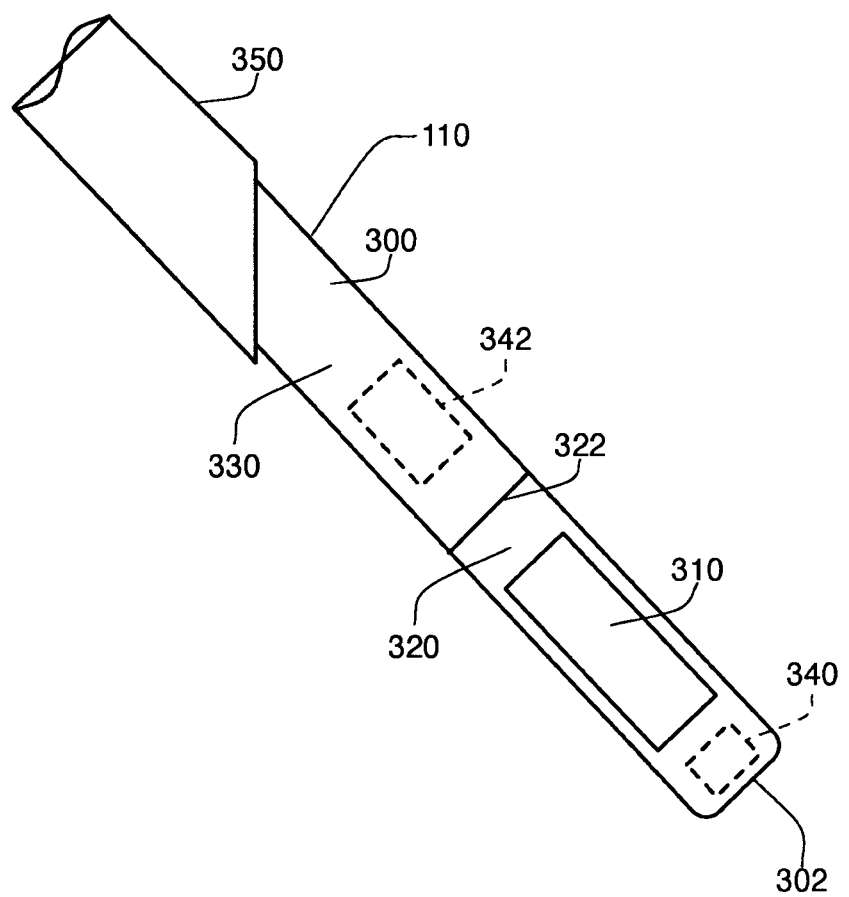
FIG. 3 is a plan view of a distal tip of a second embodiment of an EBUS device.

An alternative embodiment ultrasound catheter 300 is shown in FIG. 3 with a linear transducer array 310 proximal the tip 302 of the catheter 300. The linear transducer array 310 may be flat, and in one embodiment the linear transducer array 310 is located on a flat surface 320 of the tip of the ultrasound catheter 300. In this way, the ultrasound catheter 300 differs from the EBUS device 110 shown in FIGS. 1 and 2 that has a curved array of ultrasound transducers 112. Nonetheless, the ultrasound catheter 300 also comprises an EBUS device 110. The flat surface 320 may extend throughout the length of the catheter 300, or it may terminate at position 322. Location 322 separates the tip portion having the flat surface 320 from the remaining portion 330 of the catheter 300. The remaining portion 330 can therefore have a circular or generally rounded cross-section for ease of movement within an introducer catheter 350. The cross-section of the tip portion having the flat surface 320 may be semi-circular, with a rounded bottom portion (not shown) topped by the flat surface 320 holding the linear transducer array 310. The catheter 300 may also contain embedded electromagnetic (EM) sensors 340 at distal end 302. These EM sensors 340 function as described above in connection with sensors 116. An electronics package 342 can be coupled to the linear transducer array 310 and the EM sensors 340 to control the signals sent to and received from these components.

The ultrasound transducers 112, 310 in the EBUS device 110 can be constructed according to the disclosures filed as U.S. Provisional Application Nos. 62/776,667 and 62/776,677, which were both filed by the owner of this application, on Dec. 7, 2018. The entire contents of these two provisional applications are hereby incorporated by reference. These ultrasound transducers 112, 310 may be micromachined ultrasound transducers (or MUTs), such as a piezoelectric MUT (or pMUT), capacitive MUT (or cMUT), with pMUT transducers frequently using a lead zirconate titanate (or PZT) piezoelectric layer. These types of transducers are able to transmit and detect varying frequencies of ultrasound energy, such as frequencies running from 4 to 50 MHz.

Figure 4:
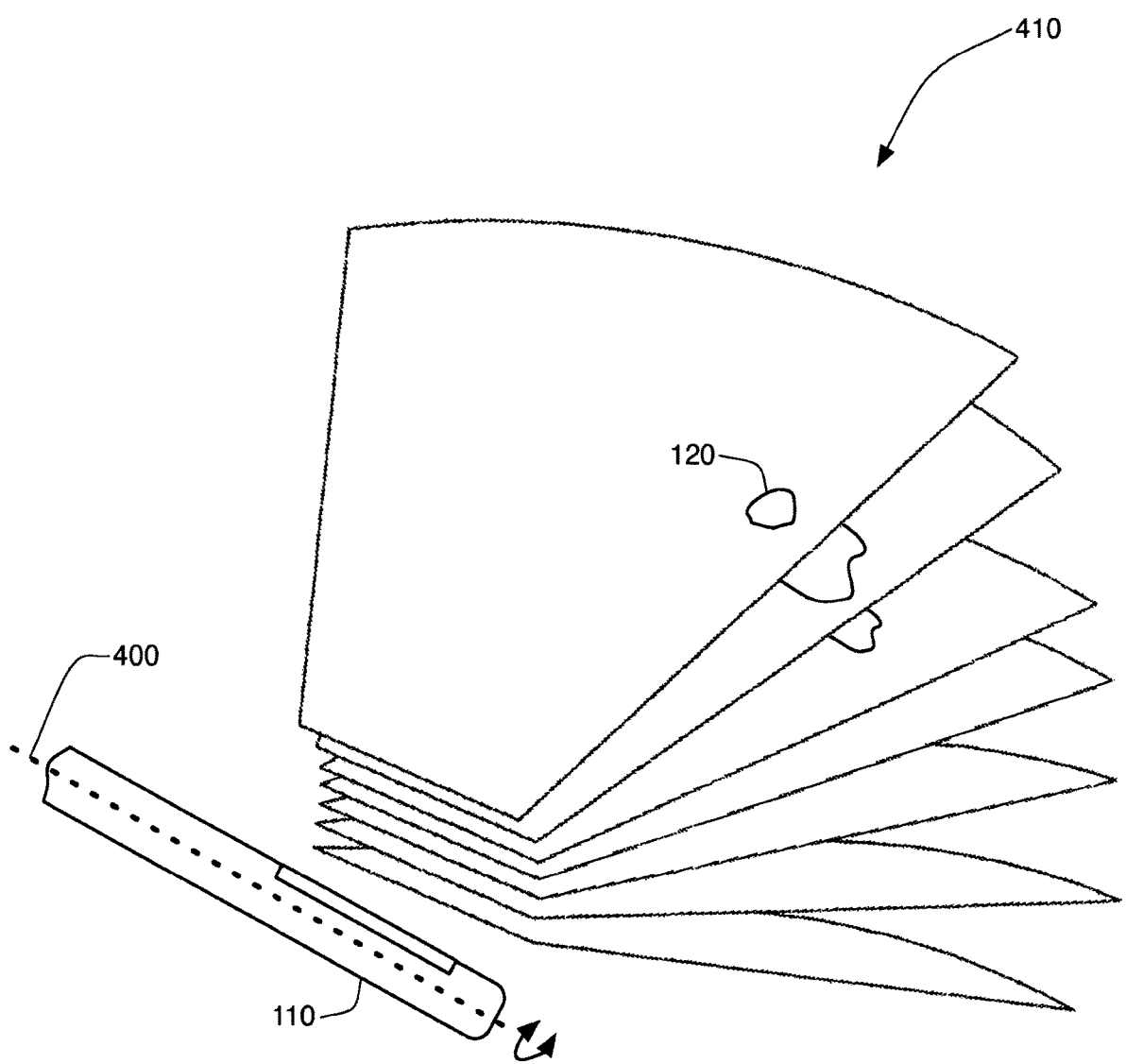
FIG. 4 is a schematic illustration of an EBUS device creating a plurality of slices through rotation.

FIG. 4 shows a generically constructed linear EBUS device 110 that can be rotated in position around a rotational access 400. FIG. 4 also shows various image area slices 410 that are separately created in different rotational positions for the EBUS device 110. Each of these slices 410 effectively defines a two-dimensional image plane created by the EBUS device 110. During use, the EBUS device 110 can be rotated around rotational access 400 by the physician performing the procedure, either manually or through the use of a rotational stepping motor (not shown in the figures). A motorized rotation could assist in creating enough slices 410 to allow for a "live" 3D ultrasound image generation. The roll sensor on the EBUS device 110 can determine the particular orientation of an image slice 410.

As shown in FIG. 4, multiple slices 410 might contain data showing the targeted tissue 120. The computer systems 140 receive image data from the EBUS device 110 representing each of these separate image slices 410. While these separate slices can be saved by the computer systems 140 and displayed when requested, the computer systems 140 are also capable of combining the information within the multiple slices 410 into a single model of the portion of the patient shown in these slices 410, including a model of the targeted tissue 120. This model can then be shown to the physician as a 3D image of the area. The generated model can also be incorporated into the previously created 3D model of the patient 100.

Monitoring Cryoablation

Figure 5:
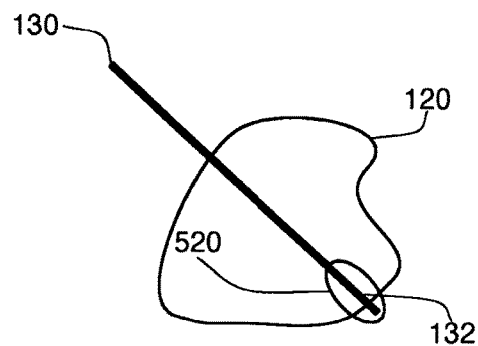
FIG. 5 is a side schematic illustration the cryoprobe of FIG. 1 penetrating the targeted tissue and generating an ice ball.

The EBUS device 110 is able to identify and locate the targeted tissue 120 and track the insertion of the cryoprobe 130 into such targeted tissue 120, as shown in FIGS. 1 and 2. In addition, the EBUS device 110 can also monitor the cryoablation process itself. This process begins after the tip 132 of the cryoprobe 130 is inserted into the targeted tissue 120, as shown in FIG. 5. After this, argon gas is passed through the probe 130. The design of the probe 130 causes the gas to expand at or near the tip 132. Since argon gas cools upon expansion, this expansion causes very rapid cooling of the tip 132 of the probe 130. In traditional cryoprobes 130, the injection of argon gas will cause the tissue proximal to the tip 132 to reach a temperature between −160 and −170 degrees Celsius (° C.). This temperature will quickly cause an ice ball 520 of frozen tissue to form adjacent to the tip 132 and expand into the targeted tissue 120.

Figure 6:
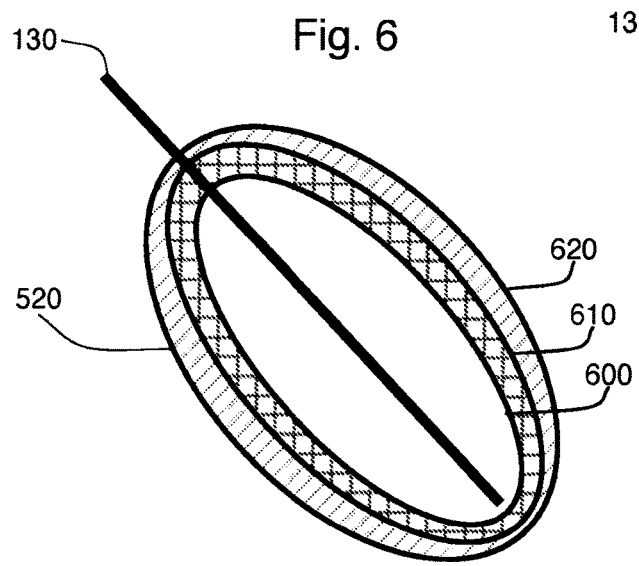
FIG. 6 is a schematic illustration of a generated ice ball with three isotherms illustrated.

While the temperature of the formed ice ball 520 near the probe may be below −160° C., the surface temperature of the ice ball 520 will remain at 0° C. To ensure destruction of the tissue, it is generally accepted that the tissue should reach a temperature of −40° C. or colder for approximately three minutes. This temperature will cause intracellular ice formation, which is destructive to most cells. Consequently, the abnormal tissue is typically frozen for three to five minutes during a cryoablation procedure. At this point, the ice ball 520 will have increased in size, as is shown in FIG. 6. After this time period, at least half of the diameter of the ice ball 520 will have reached −40° C. This is shown schematically in FIG. 6 by central area 600. The wider shaded region 610 shows the approximate location of the −20° C. isotherm, while the outer surface 620 of the ice ball 520 will have a temperature of −0° C.

Because only that portion of the ice ball 520 that has had a sustained temperature of −40° C. can be assured to have been destroyed, most cryoablation practitioners perform the procedure twice. After first forming the ice ball 520, the ice ball is allowed to thaw. The slow thawing of the frozen tissue in the ice ball 520 will cause further cell damage, as the thawing ice crystals will fuse to form larger crystals that cause further cell damage. The thawing process can be expedited by passing helium through the cryoprobe 130. Unlike cryogen gasses like argon, helium warms upon expansion. When helium passes through the cryoprobe 130, it will have the opposite effect of argon and will heat the tip 132 of the cryoprobe 130.

Figure 7:
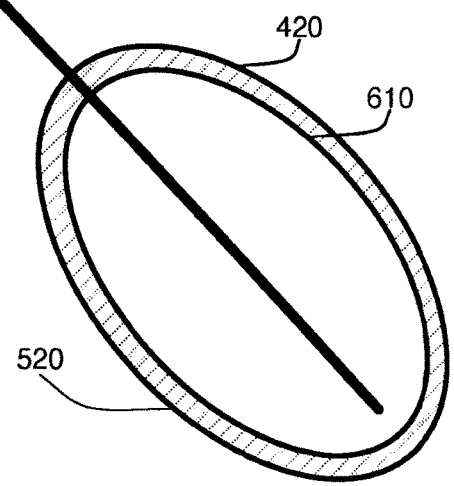
FIG. 7 is a schematic illustration of the generated ice ball of FIG. 3 after a second freeze.

The standard technique of freezing the abnormal tissue a second time after thawing will cause the freezing of the tissue to occur more rapidly (which is more destructive to the tissue). This allows complete tissue destruction at slightly warmer temperature, such as between −20° C. and −30° C. As a result, the effective treatment area of the procedure moves closer to the periphery 420 of the ice ball 520. As shown in FIG. 7, the central kill area will expand approximately to the −20° C. isotherm line 610. In most circumstances, the distance between the kill area and the periphery of the ice ball is believed to be between 4 and 10 mm. Because the outer areas of the ice ball 520 will be outside the assured treatment area 610, it is generally required to create an ice ball during cryosurgery that is larger than the tissue 120 desired to be destroyed.

Figure 8:
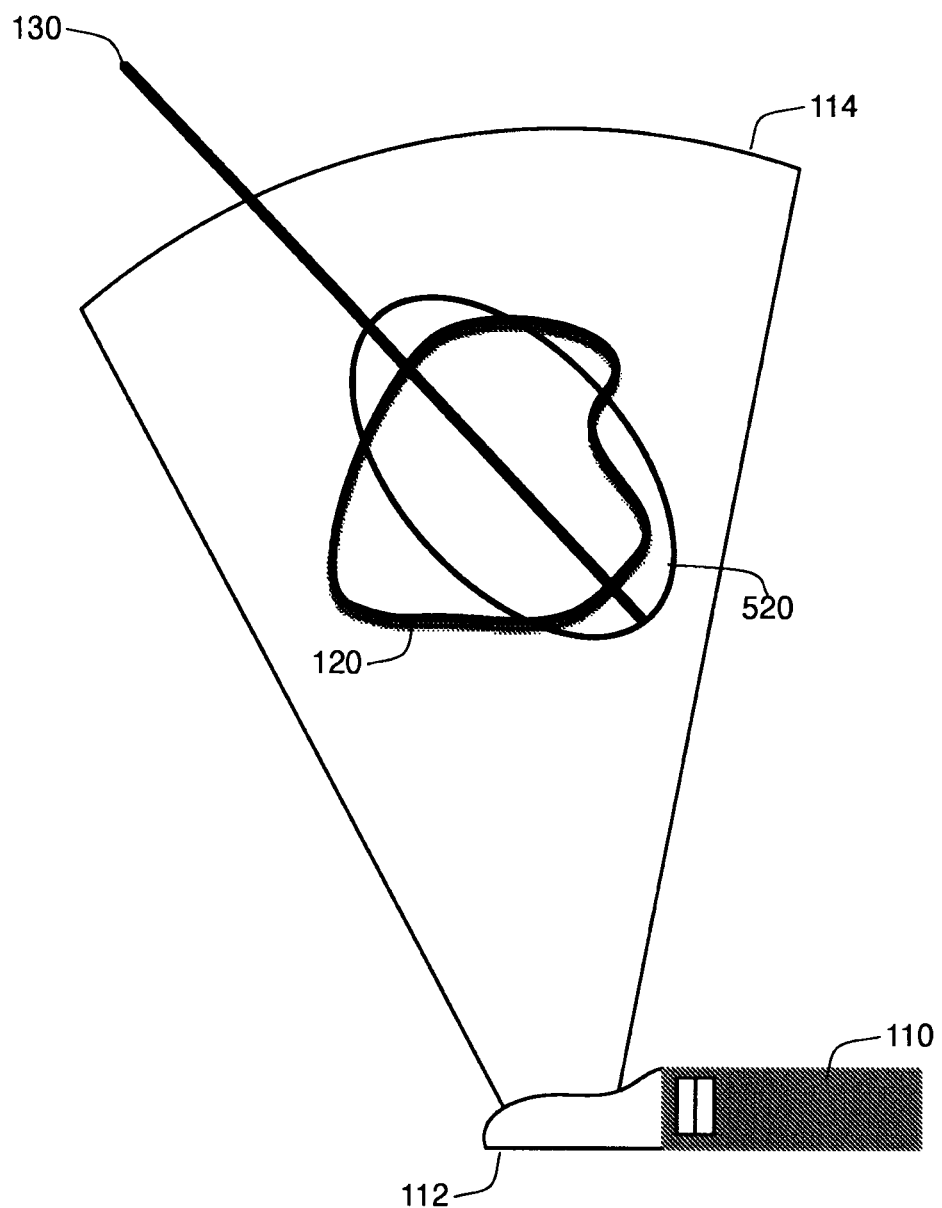
FIG. 8 is a schematic illustration of the EBUS device of FIG. 2 having an idealized view of an ice ball being formed in targeted tissue.

FIG. 8 shows an idealized view of monitoring the cryoablation procedure using the EBUS device 110. The image area 114 of the EBUS device 110 includes the tissue 120. The cryoprobe 130 will be monitored as it is inserted percutaneously into the targeted tissue 120, and the ultrasound transducers 112 will then track the formation of the ice ball 520.

Figure 9:
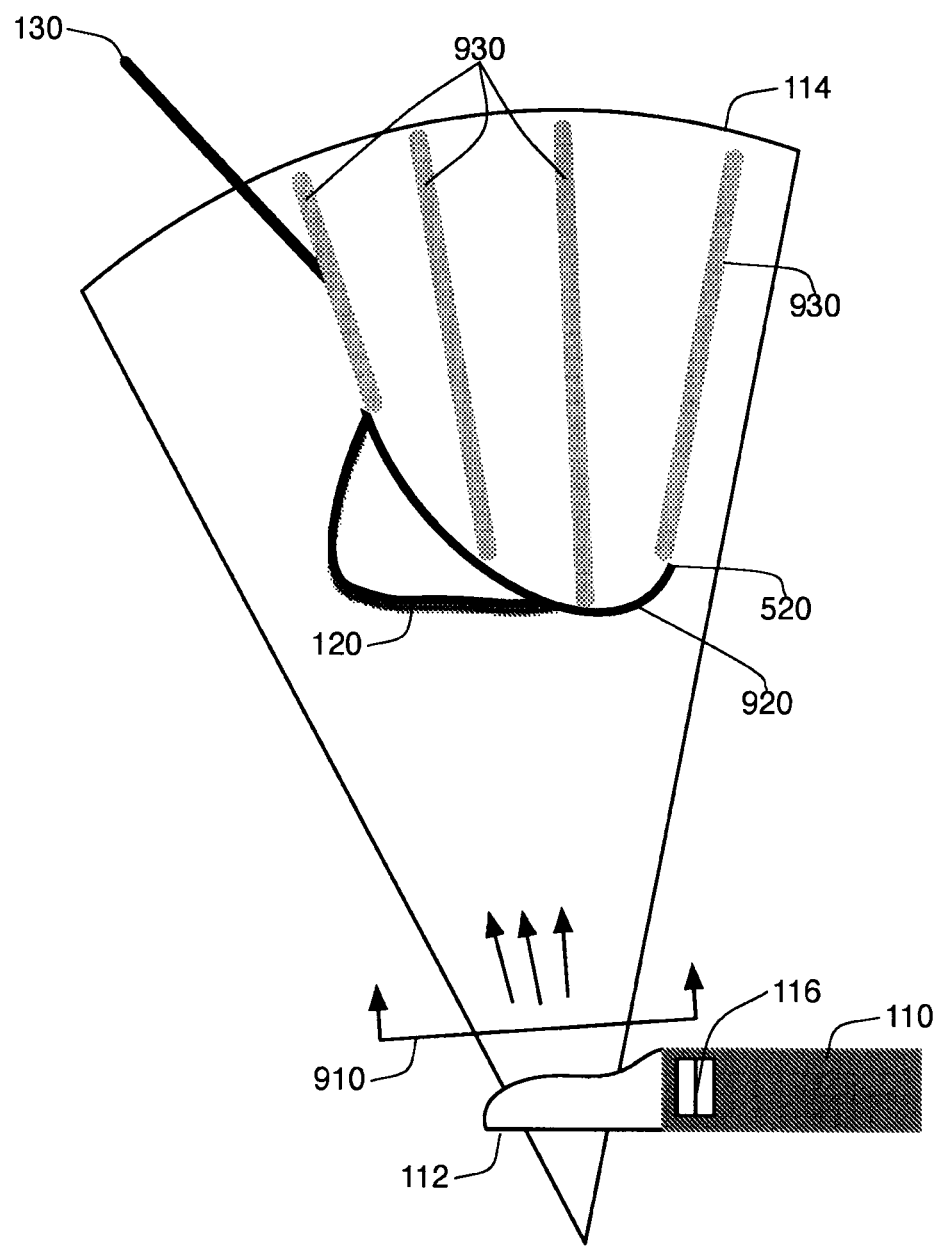
FIG. 9 is a schematic illustration of the EBUS device of FIG. 2 viewing an ice ball being formed in targeted tissue in the context of an acoustic shadow.

Unfortunately, this idealized view is not reality, as the frozen nature of the ice ball 520 makes it extremely echogenic to ultrasound energy. In effect, the different physical characteristics between the thawed and frozen tissue, including the change in density of the tissue and the resulting change in the speed at which sound travels through the tissue, creates an acoustic impedance mismatch that causes substantially all of the ultrasound energy to bounce off the ice ball 520. In addition, the ice ball 520 itself will absorb ultrasound energy much more efficiently than unfrozen tissue. Thus, as shown in FIG. 9, while the reflective nature of the ice ball 520 creates a clear image of the ice ball surface 920 nearest to the ultrasound transducers 112, the ultrasound energy cannot effectively penetrate beyond this surface 920. This creates an acoustic shadow 930 behind this surface 920 which prevents any tissue or structure behind the surface 920 from appearing in the resulting ultrasound image. This acoustic shadow 930 is shown in the figures as shadow lines 930. Elements that do not fall within the acoustic shadow 930 can still be seen in the image area 114, which in FIG. 9 includes a portion of the targeted tissue 120 and a portion of the cryoprobe 130.

FIG. 9 shows a single image area 114 at a particular time. As explained above, however, multiple slices 410 can be created by rotation of the EBUS device 110, and these slices can be joined together into a 3D image or model. Each slice 410 that contains the ice ball 520 will also be subject to the acoustic shadow 930. Thus, the 3D image/model will show only the surface 920 of the ice ball 520 seen from the point of view 910 established by EBUS device 110. This means that the practitioner will be able to see that the ice ball 520 was formed by the cryoprobe 130, and that a portion of the targeted tissue 120 remains unablated on this side of the ice ball surface 920. However, since the practitioner cannot see into the acoustic shadow 930 created beyond the closest surface 920 of the ice ball 520, she cannot confirm whether the distal portion of the targeted tissue 120 was properly ablated.

Figure 10:
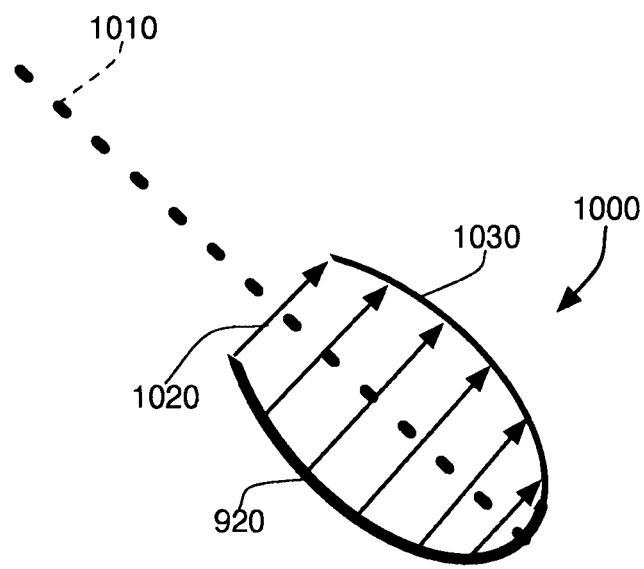
FIG. 10 is a schematic illustration showing the formation of an ice ball model through mirroring in a side view.

While it is possible to wait for the ice ball 520 to melt before imaging the ablated tissue, waiting for melting would not provide any useful guidance during the freezing process as to whether the process should continue for additional time. To overcome this limitation, an approximation 1000 can be made of the ice ball 520, as shown in FIG. 10. The approximation 1000 is created by the computer systems 140 based on the information obtained by the EBUS device 110 about the surface 920 of the ice ball 520 that can be seen. This surface 920 is shown in FIG. 10 along with an axis 1010 for the cryoprobe 130. This axis 1010 is created by examining the six DoFs sensors for the cryoprobe 130. This information can identify the location and orientation of the tip 132 of the cryoprobe 130, which is then used to define the axis 1010 within the same 3D space as the identified surface 920.

Once the axis 1010 is identified, the individual locations in 3D space of the visible surface 920 are reflected across the axis 1010 as shown by arrows 1020. In 2D space, this reflection creates the opposite approximation of the non-seen surface 1030. To accomplish this locations on the visible surface 920 are compared with the axis 1010. A line segment perpendicular to the axis 1010 is identified between the axis 1010 to the point on the peripheral surface. An opposite line segment of the same length is then used to approximate a point on the hidden, non-visible side of the ice ball. Sufficient points are "mirrored" across the cryoprobe axis in order to define an approximate location for a large segment of the hidden, non-visible periphery. This is then combined with the points on the visible surface to create a model of the ice ball.

Figure 11:
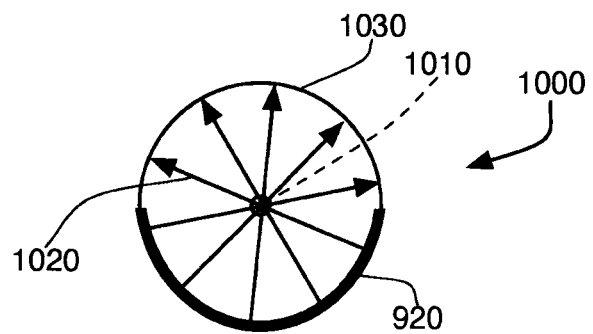
FIG. 11 is a schematic illustration showing the formation of an ice ball model through mirroring in an axial view.

Note that this mirroring or reflection is conducted in 3D space. FIG. 11 shows the reflection 1020 of individual points across the axis 1010 when viewed axially down axis 1010. The non-seen surface 1030 is created by the reflection 1020 process and is then combined with the visible surface 920 to define the model 1000 of the ice ball 520.

Figure 12:
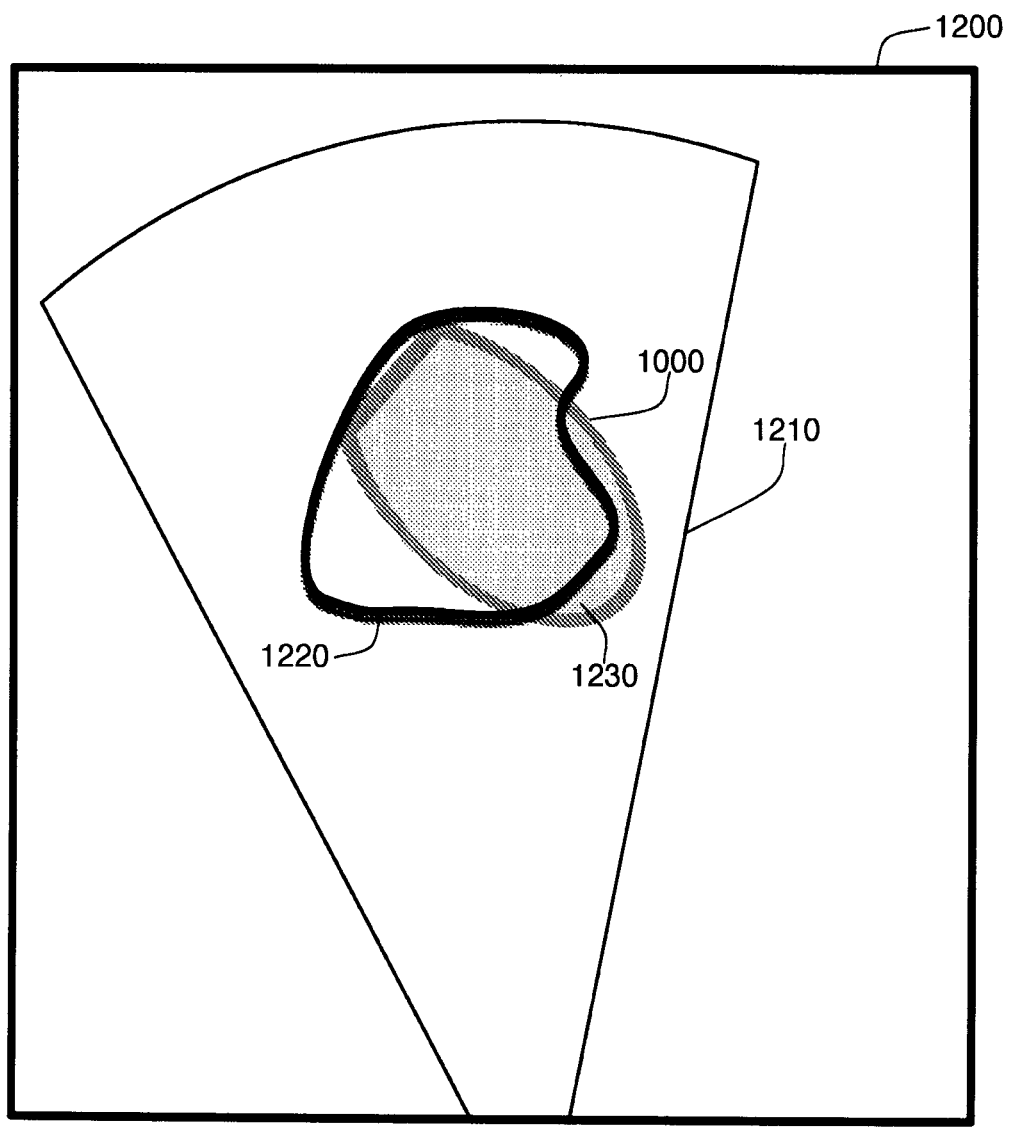
FIG. 12 is a user interface showing the ice ball model of FIGS. 10 and 11, and the location of the targeted tissue.

This model 1000 can then be presented to the practitioner through a user interface 1200 created by the computer systems 140 on the display 150, as shown in FIG. 12. This user interface 1200 can present the 3D model 1000 through known visualization techniques, although interface 1200 shows only a 2D slice view of the model 1000 in order to simplify the discussion of this figure. The model 1000 is shown within a representation 1210 of the live image area 114 of the EBUS device 110. The computer systems 140 have full knowledge of the location of the targeted tissue 120, so an abnormal tissue location 1220 is also presented within the same space as the ice ball model 1000. In this way, the practitioner is able to see the ice ball 520 on a live interface 1200 and is able to compare the current size, shape, and location of the ice ball 520 with respect to the targeted tissue 120. As the ice ball 520 grows in size during the freezing process, the surface 920 seen by the ultrasound transducers 112 will grow as well. The computer systems 140 will identify this change, use the new positions of the surface 920 in the reflection process 1020 to adjust the approximation of non-seen surface 1030, and then present the revised model 1000 in near real-time on interface 1200.

Note that the model 1000 of the ice ball 520 is not able to recreate the rounded portion of the ice ball 520 that is distal to the tip 132 of the cryoprobe 130. Not enough information is available in the visible surface 920. As a result, the model 1000 of the ice ball 520 has a flattened portion instead. This is not a requirement of the modeling process, but it does show the limit of the reflection process 1020. The modeling steps could include an additional step to create a more rounded portion distal from the tip 132 based on actual observations and the diameter of the flattened portion.

In one embodiment, interface 1200 is presented on a live view of the visual information seen by the ultrasound transducers 112. Thus, a standard ultrasound screen is seen in live mode up to the visual surface 920 of the ice ball 520. Instead of showing the acoustic shadow 930 in the interface, however, the computer systems 140 superimpose a portion of the abnormal tissue location 1220 and the model 1000 to represent the unseen portion of the ice ball 520 and the targeted tissue 120. This can be done with either a 2D live ultrasound image or a 3D live ultrasound image.

As explained above in connection with FIGS. 6 and 7, the outer surface of the ice ball 520 is not as important to the practitioner as the −40° C. isotherm 600 during the first freezing process and the −20° C. isotherm 610 during the second freezing process. As these two boundaries define the area of tissue that can be considered fully ablated. This boundary is shown in interface 1200 as the inner isotherm 1230. The computer systems 140 can monitor the cryoablation process including the freezing and thawing of tissue. Thus, the computer system 140 will have knowledge as to whether the current freezing process is the first freezing (which would mean the −40° C. isotherm 600 is the effective ablation region) or the second freezing (which would mean the −20° C. isotherm 610 is the effective ablation region). Whichever is selected, the approximate effective ablation region 1230 is also included in the interface 1200. This allows the practitioner to continue the freezing process as appropriate to ensure that the entire targeted tissue 120 is fully ablated. Alternatively, the practitioner can see that continued freezing is not appropriate, and that unablated targeted tissue 120 should be ablated after repositioning the cryoprobe 130 or after the placement of an additional cryoprobe 130.

Process 1300

Figure 13:
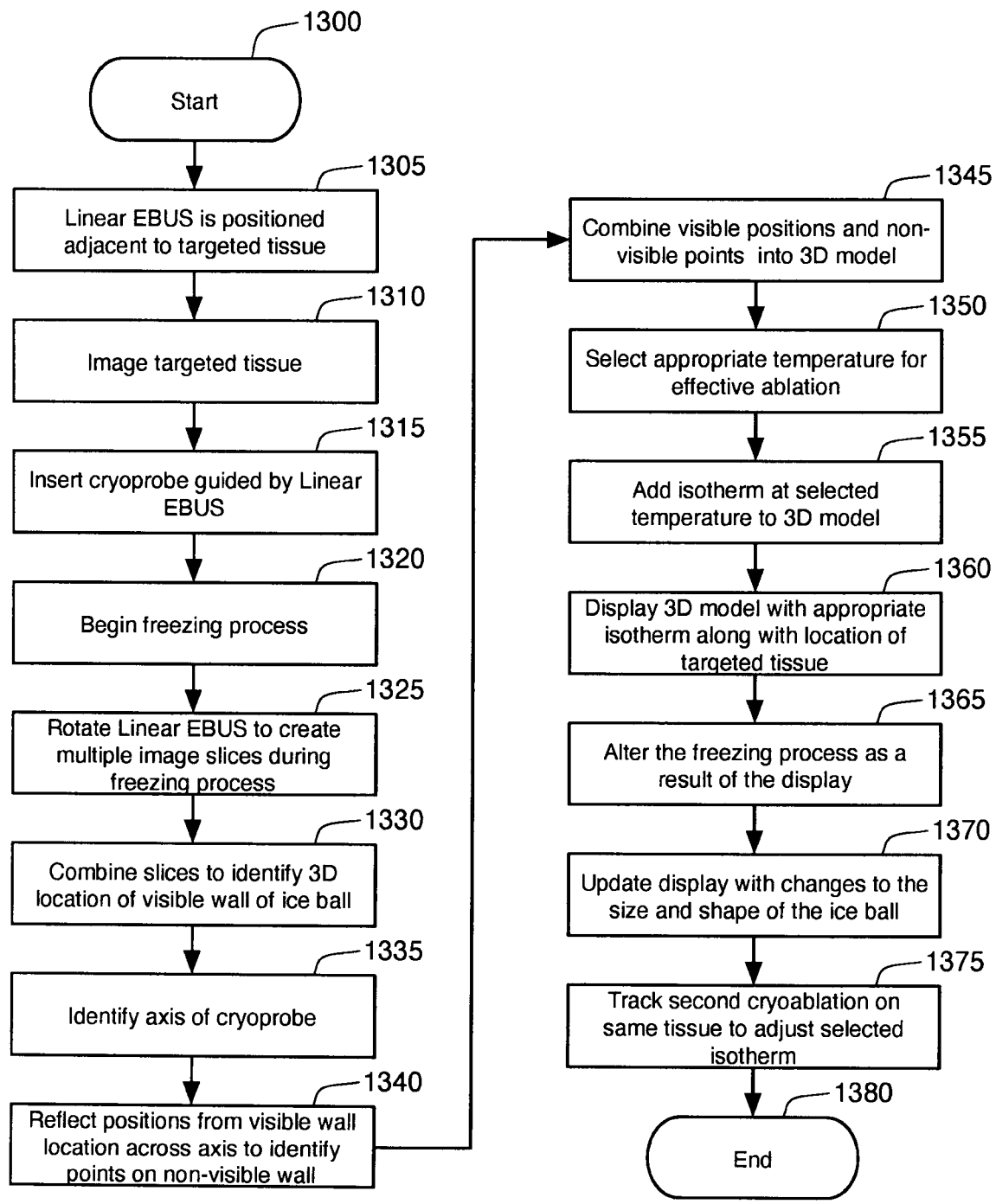
FIG. 13 is a flow chart showing a method for implementing one embodiment of the present disclosure.

The individual steps described above can be combined into process or method 1300, as shown in the flow chart of FIG. 13. Before this method begins, a 3D model of the patient is created using standard imaging methodologies, such as CT or MRI scanning. The patient is then registered to this 3D model through the creation of an electromagnetic field around the patient and the use of EM sensors.

The first step 1305 in method 1300 is to position the EBUS device 110 into the trachea-bronchial tree of the patient 100 so that it is located adjacent the targeted tissue 120. At step 1310, the ultrasound transducers 112 of the EBUS device 110 will image the targeted tissue 120. This image data can be integrated into the 3D model of the patient. Location information taken from the EM sensors 116 on the EBUS device 110 may provide sufficient details as to the location of the targeted tissue 120 that it is possible to fine tune the registration between the 3D model and the patient at this point.

At step 1315, the cryoprobe 130 is inserted percutaneously into the targeted tissue 120. In some cases, as described in more detail below, multiple cryoprobes 130 may be inserted into the targeted tissue 120 in order to create an ice ball 1430 of different shapes and sizes. This insertion can be guided by the image data acquired by the ultrasound transducers 112. This live image data can be displayed by the computer systems 140. At this time, the EBUS device 110 can be rotated in order to create multiple image slices 410, as explained above in connection with FIG. 4. These multiple slices can be combined together at step 1330 to create 3D image and model of what is captured by the ultrasound transducers 112 of the EBUS device 110.

At step 1320, the freezing of the targeted tissue 120 is initiated using the cryoprobe 130 while still being monitored by the ultrasound transducers 112. This is accomplished at step 1325. The EBUS device 110 is able to monitor the formation of the ice ball 520 and its location relative to the targeted tissue 120. Because of the nature of the ice ball 520 being formed, the EBUS device 110 will not be able to form an image beyond the visible surface 920 of the ice ball 520 because of the acoustic shadow 930 created by the ice ball's frozen outer surface 620. Nonetheless, basic ultrasound imagery created by steps 1305-1330 can be very useful in monitoring the cryoablation procedure.

To overcome the issue of the acoustic shadow 930, step 1335 identifies the axis 1010 of the cryoprobe 130. More particularly, the location and orientation of the tip 132 of the cryoprobe 130 is used to form this axis 1010. This location and orientation are determined by analyzing the EM sensors on the tip 132 of the cryoprobe 130. At step 1340, individual positions in 3D space are identifies on the visible surface 920 of the ice ball 520. These 3D positions are then reflected across the axis 1010 to identify points on the hidden surface 1030. This reflection is taken perpendicularly to the axis 1010, with the non-seen surface 1030 being considered to be formed at the reflection points on the other side of the axis 1010 at a point equally distant from that axis 1010 as the point on the visible surface 920. At step 1345, the 3D positions of the visible surface 920 are combined with the determined points on the hidden surface 1030 to form a 3D model 1000 of the ice ball 520. Not all points on the visible surface 920 need to be mathematically reflected in this way-only a representative sample sufficient to identify the shape of the ice ball 520. The 3D model 1000 can approximate positions in between the selected 3D positions on the visible surface and reflected points on the hidden surface.

At step 1350, it is necessary to select an appropriate temperature for effective ablation. As explained above, only that portion of the ice ball 520 that has had a sustained temperature of −40° C. can be assured to have been destroyed during the first freezing of the tissue. Consequently, if this is the first freezing, the −40° C. temperature is selected. If this were the second freezing, complete tissue destruction is considered to occur at a warmer temperature, such as between −20° C. and −30° C. Thus, if this is the second freezing, a warmer temperature is selected at, perhaps, −25° C. An isotherm 1230 for the selected temperature is then added to the model 1000 of the ice ball 520. This isotherm 1230 must be approximated based on the known temperature variations at the edge of an ice ball 520 during cryoablation. For example, it is generally accepted that the distance between the periphery of the ice ball 520 and the −40° C. killing zone is 10 mm or less. Appropriate testing can establish a direct relationship between the distance inside the ice ball 520 and the temperature of the tissue at that location. This testing should be done during an active freezing session, as temperature curves within an ice ball could be altered significantly after the freezing process has terminated or, for instance, during the active thawing process. As an example, the −40° C. isotherm could be considered to exist at 8 mm inside the periphery of the ice ball 520, while the −25° C. isotherm is considered to exist at 5 mm inside the periphery of the ice ball 520. At step 1355, this selected isotherm is added to the model 1000 of the ice ball 520.

In some embodiments, the selected isotherm is not added to the model 1000 of the ice ball 520 until after the identified temperature has been sustained for a given time period. As explained above, a temperature of −40° C. must be sustained for three minutes in order for the tissue to be considered fully ablated, at least during a first freezing process according to current understandings. The computer systems 140 can use the distances identified in the previous paragraph to monitor which portions of the ice ball 520 have achieved this temperature, and then add the selected isotherm to the model 1000 only after the temperature has been sustained for the appropriate time.

At step 1360, the computer systems 140 will present interface 1200 to the practitioner. More particularly, the location of the model 1000 of the ice ball 520 will be shown in user interface 1200 along with the location of the selected isotherm 1230 and the modeled location 1220 of the targeted tissue 120. It is possible that live ultrasound image will also be presented on this interface 1200 up to the visible surface 920 of the ice ball 520. The ice ball model 1000, the selected isotherm 1230, and the modeled location 1220 of the targeted tissue 120 will then be shown in the area that constitutes the acoustic shadow 930. The ultrasound image can also be supplemented to highlight the visible surface 920 of the ice ball 520 and the visible outline of the targeted tissue 120.

In some embodiments, programming on one or more of the computer systems 140 compare the model 1000 of the ice ball, or more particularly the created selected isotherm 1230, against the size and shape of the abnormal tissue location 1220. The programming will then identify portions of the targeted tissue outside the selected isotherm 1230 (which defines an effective treatment area for the area of ablated tissue) and then alter the user interface 1200 so as to visually emphasize those portions of the abnormal tissue location 1220 that is outside of this effective treatment area. This visual emphasis can be accomplished through a variety of visual characteristics. For example, the user interface 1200 may use a different color, a different intensity, or a flashing or other periodic alteration of the display to distinguish those portions.

At step 1365, the practitioner then changes their planned freezing process as a result of the display of user interface 1200. For example, the user interface 1200 may show that the entire targeted tissue 120 is likely fully ablated by showing the abnormal tissue location 1220 completely encompassed by the selected isotherm 1230. Consequently, the freezing process can be terminated earlier than otherwise anticipated. The prevention of excess freezing prevents healthy tissue from being ablated. Alternatively, the user interface 1200 may show that additional freezing beyond what was anticipated is needed to fully ablate the targeted tissue 120 when the selected isotherm 1230 fails to encompass the abnormal tissue location 1220.

Step 1370 indicates that this interface 1200 is updated in near real-time during the freezing process so that the practitioner has the knowledge necessary to know whether the current freezing process can stop, or whether it should continue in order to fully ablate the targeted tissue 120.

Step 1375 indicates that this method 1300 can be used over multiple freezing cycles. As explained above, step 1350 will select the appropriate temperature for the current state of the overall ablation procedure. This requires that method 1300 be able to recognize when a first freezing process has stopped, the first ice ball 520 has thawed, and a second freezing process is begun. This occurs at this step 1375. Such identification is relatively simple to program into the computer systems 140 as the steps described above are designed to identify the periphery of the ice ball 520. Thus, after the ice ball 520 is detected, grows, and disappears, the computer systems 140 will know that the appearance of a new ice ball 520 will be the result of a second freezing process. The method 1300 then ends at 1380.

Note that steps 1370 and 1375 are shown in FIG. 13 as occurring temporally after the other steps of method 1300. This is not how these steps are actually implemented. For example, the updating of step 1370 will require the continual performance of steps 1325-1365, while the second freezing on the same tissue detected at step 1375 will be conducted during the continuing performance of steps 1320-1370. These steps 1370, 1375 are presented at the end of method 1300 merely to provide a visual indication that these elements 1370, 1375 form part of the other steps of method 1300.

Multiple Cryoprobe Applications

Figure 14:
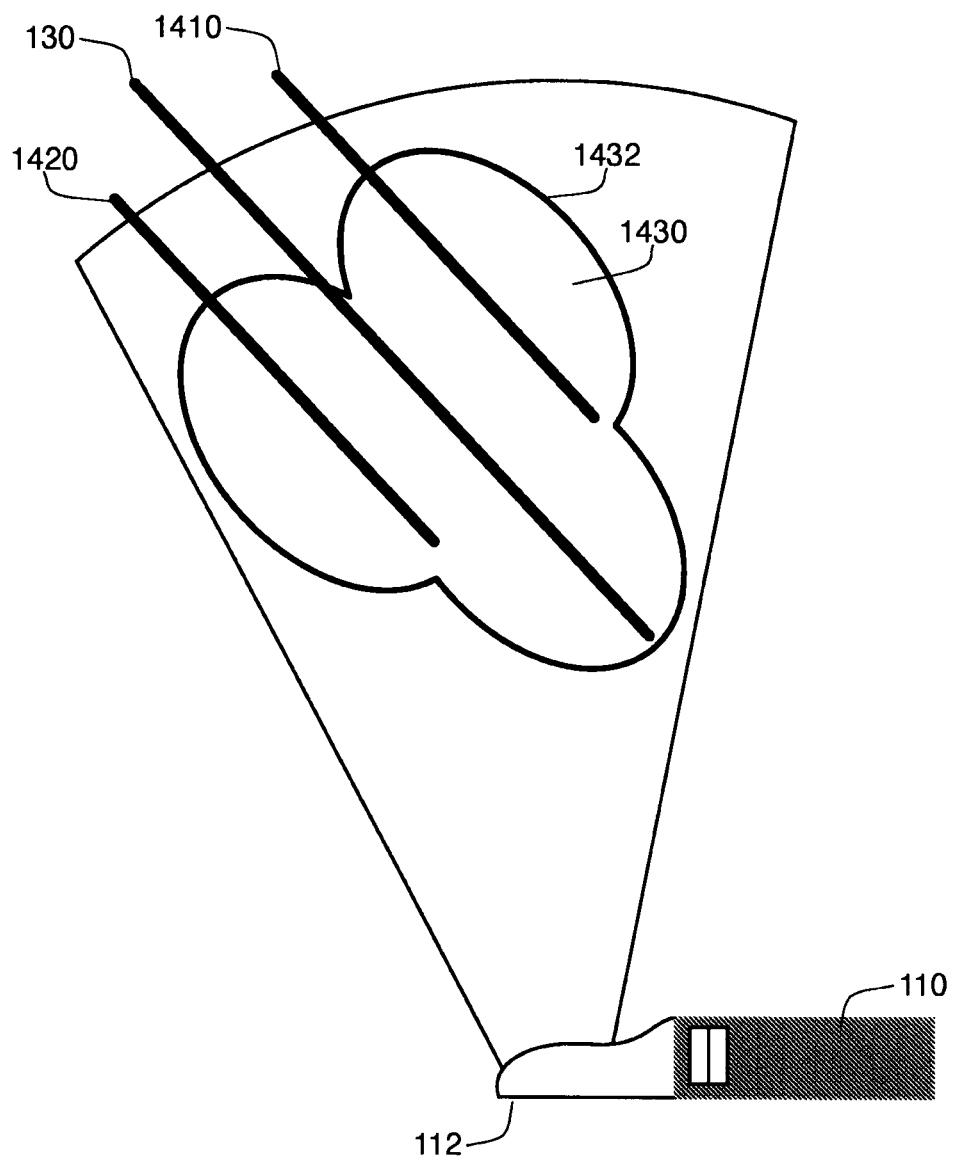
FIG. 14 is a schematic illustration of the EBUS device of FIG. 2 having an idealized view of an irregular ice ball.

In some circumstances, it is necessary to create a different shape to the ice ball in order to match the shape and size of the targeted tissue 120. In this circumstance, multiple cryoprobes can be inserted into different portions of the tissue 120. In FIG. 14, the first cryoprobe 130 is joined by a second cryoprobe 1410 and a third cryoprobe 1420. While these cryoprobes 140, 1410, and 1420 may be inserted into the targeted tissue 120 using an introducer cannula, this is not necessary. When the three cryoprobes 140, 1410, 1420 are cooled, they work together to create a single ice ball 1430 with a unified, but irregularly shaped surface 1432. It is possible that some of the cryoprobes 140, 1410, 1420 will operate at different temperatures, with slightly warmer temperatures having a smaller freezing impact. Furthermore, the manufacturing of the cryoprobes 140, 1410, 1420 can influence the resulting shapes of the ice balls (with some probes creating a more spherical shape, for instance). By using differing designs and temperatures between the cryoprobes 140, 1410, 1420, it is possible to intentionally conform the resulting ice ball 1430 into a shape that more effectively kills the targeted tissue 120 while minimizing damage to surrounding tissue.

The process of monitoring the formation of this irregularly shaped ice ball is the same process 1300 described above. Steps 1305-1325 can be used to monitor the insertion of the cryoprobes and the freezing process. However, the irregular shape of this ice ball 1430 makes it less likely that the reflection process will create a model that accurately reflects the shape of this ice ball 1430. However, if the multiple cryoprobes 130, 1410, 1420 are approximately on the same plane as the ultrasound transducers 112 of the EBUS device 110, and are used in a symmetrical pattern around the axis of the central cryoprobe 130, then the process 1300 can be applied.

Figure 15:
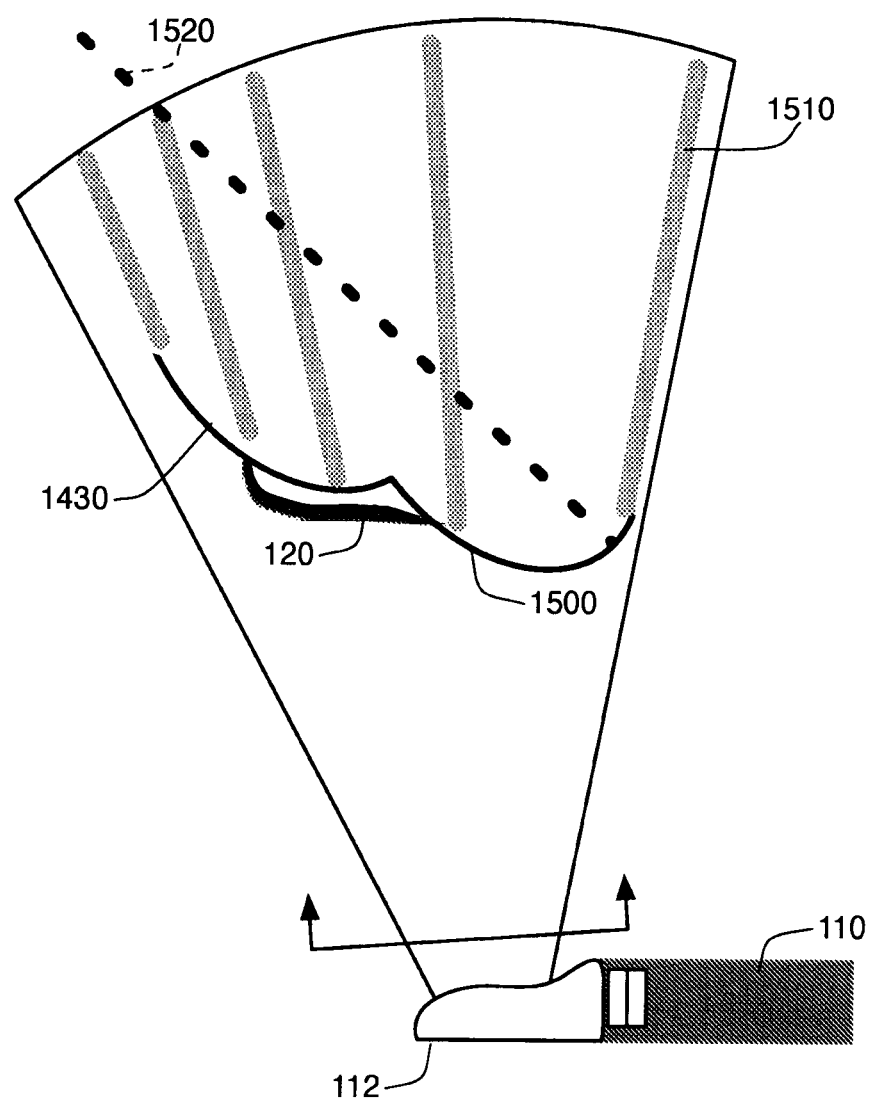
FIG. 15 is a schematic illustration of the EBUS device of FIG. 2 viewing an irregular ice ball in the context of an acoustic shadow.
Figure 16:
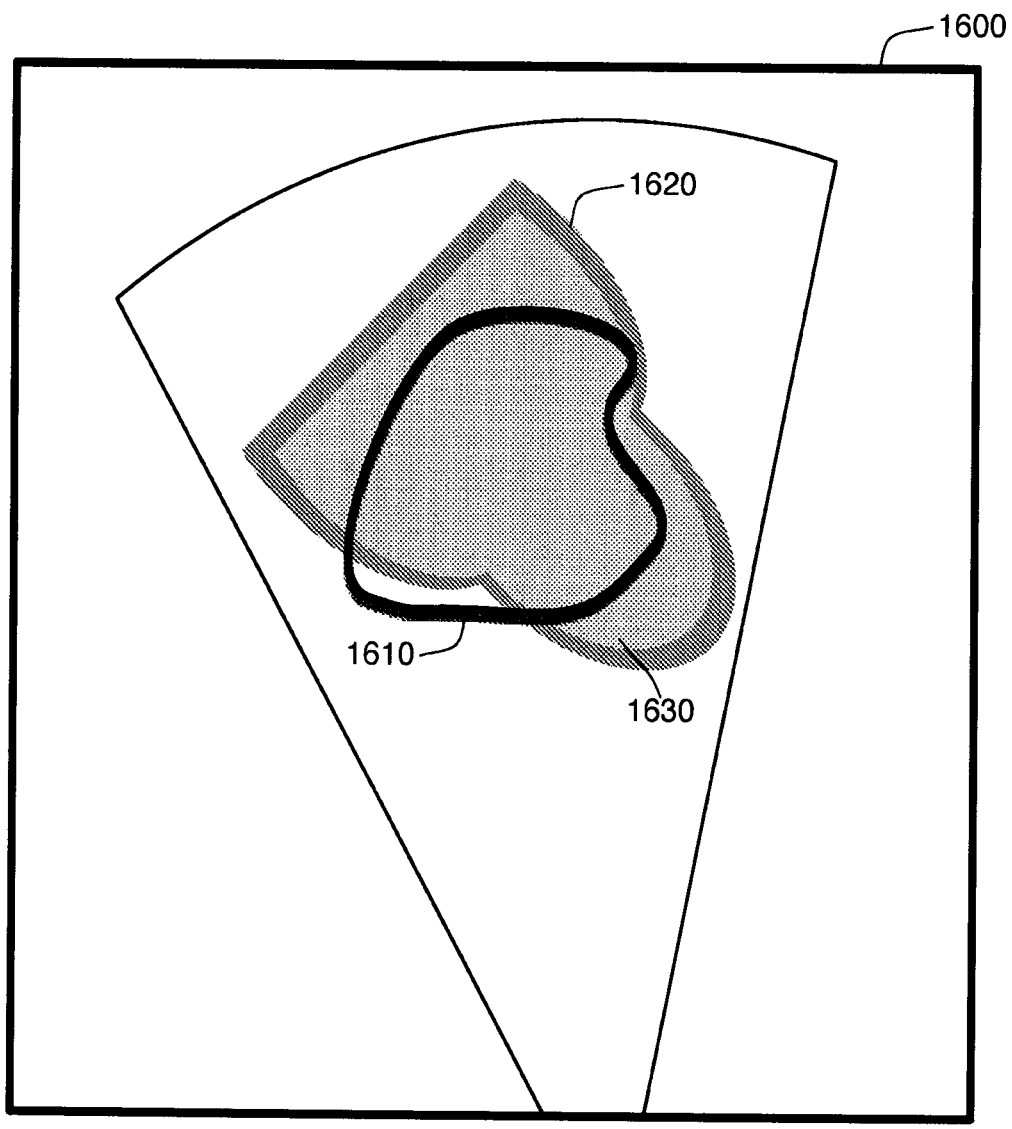
FIG. 16 is a user interface showing the ice ball model of FIGS. 10 and 11, and the location of the targeted tissue.

As shown in FIG. 15, the ultrasound transducers 112 of the EBUS device 110 can only see the proximal visible side 1500 of the created ice ball 1430. The transducers 112 can image the fact that a proximal portion of the targeted tissue 120 has not been ablated, but they have no knowledge of the far side of the ice ball 1430 because of the acoustic shadow 1510 created by the ice ball 1430. The computer systems 140 can, however, identify an axis 1520 representing the angle and location of the central cryoprobe 130. This axis can be used to generate user interface 1600, as shown in FIG. 16. This user interface 1600 shows a representation 1610 of the targeted tissue 120 and the generated model 1620 of the ice ball 1430. Furthermore, the user interface 1600 shows the selected isotherm 1630 showing the current area of affective ablation.

The process 1300 and the generated models 1000, 1620 described above are primarily designed to provide live monitoring of cryoablation procedures. After the ice ball 520 (or ice ball 1430) thaws, it is possible that the EBUS device 110 can image the thawed, ablated tissue. This tissue can be directly viewed by the ultrasound transducers 112 of the EBUS device 110, and then compared to the targeted tissue 120. But waiting for the thawing to occur means that no assistance is being provided to the practitioner during the cryoablation procedure. The methods and apparatus described above are capable of providing imagery that directly assists the practitioner during the freezing process of the procedure.

The many features and advantages of the disclosure are apparent from the above description. Numerous modifications and variations will readily occur to those skilled in the art. Since such modifications are possible, the disclosure is not to be limited to the exact construction and operation illustrated and described. Rather, the present disclosure should be limited only by the following claims.

What is claimed is:

1. A method for treating a patient comprising:
   a) placing an ultrasound device in a trachea-bronchial tree of the patient in position to image a targeted tissue;
   b) placing a cryoprobe into the targeted tissue;
   c) generating an ice ball by cooling the cryoprobe; and
   d) while generating the ice ball:
      i) rotating the ultrasound device to create multiple 2D image slices of the targeted tissue,
      ii) using a computer, combining the multiple 2D image slices to identify a visible surface of the ice ball,
      iii) using the computer, generating a 3D model of the ice ball based on the visible surface,
      iv) using the computer, generating an isotherm for the 3D model at a selected temperature identified for effective ablation, and
      v) using the computer, displaying on a user interface the 3D model of the ice ball and the isotherm.

2. The method of claim 1, wherein the ultrasound device is a linear endobronchial ultrasound (EBUS) device.

3. The method of claim 2, wherein the linear EBUS device has a plurality of ultrasound transducer elements; further wherein the plurality of ultrasound transducer elements are of a type selected from a set consisting of PZT based-transducers, pMUT based-transducers, and cMUT based-transducers.

4. The method of claim 1, further comprising displaying on the user interface a representation of the targeted tissue relative to the 3D model of the ice ball and the isotherm.

5. The method of claim 1 further comprising comparing on the computer the 3D model of the ice ball against a known size and shape of the targeted tissue to identify portions of the targeted tissue outside the isotherm; and displaying the identified portions of the targeted tissue on the user interface using an identifiable distinguishing visual characteristic.

6. The method of claim 1, wherein a distal end of the ultrasound device further contains electromagnetic sensors that receive electromagnetic signals that locate the distal end in an electromagnetic field, and further comprising using the electromagnetic signals to display on the user interface the 3D model of the ice ball on a representation of the targeted tissue.

7. The method of claim 1, wherein the 3D model of the ice ball and the isotherm displayed on the user interface change over time in response to an increase in size of the ice ball.

8. The method of claim 1, further comprising terminating generation of the ice ball prior to an anticipated termination time when the user interface indicates that the isotherm encompasses the targeted tissue.

9. The method of claim 1, further comprising continuing generation of the ice ball beyond an anticipated termination time when the user interface indicates that the isotherm fails to encompass the targeted tissue.

10. The method of claim 1, wherein generating of the 3D model comprises:
  i) identifying an axis for the cryoprobe,
  ii) identifying 3D positions on the visible surface of the ice ball,
  iii) reflecting the identified 3D positions across the axis for the cryoprobe to identify points on a hidden surface of the ice ball, and
  iv) combining the 3D positions on the visible surface with the identified points on the hidden surface.

11. The method of claim 10, wherein reflecting the identified 3D positions across the axis for the cryoprobe takes place perpendicularly from the axis and the points are equidistance from the axis as the identified 3D positions.

12. The method of claim 10, wherein only a selected number of 3D positions are reflected, and the 3D model approximates positions between the selected number of 3D positions on the visible surface and the points on the hidden surface.

13. The method of claim 1, wherein generating the isotherm for the 3D model at the selected temperature comprises:
  i) identifying a known distance from a perimeter of the ice ball known to be at the selected temperature or colder;
  ii) identifying the isotherm that is at that known distance from the perimeter of the ice ball.

14. The method of claim 13, wherein in the known distance is determined through testing of temperatures in cryoablation tests.

15. The method of claim 13, further comprising requiring that the selected temperature or colder be sustained for a determined time period.

16. The method of claim 15, wherein the determined time period is at least three minutes.

17. A system comprising:
  a) a cryoprobe;
  b) an ultrasound device;
  c) a display;
  d) a computer system in communication with the cryoprobe, the ultrasound device, and the display, the computer system having a processor operating under programming, the programming causing the computer system to:
    i) receive 2D image slices of targeted tissue in a patient from the ultrasound device as it rotates within the patient, the 2D image slices containing representations of an ice ball as being formed by the cryoprobe,
    ii) combine the 2D image slices to identify a visible surface of the ice ball,
    iii) generate a 3D model of the ice ball based on the visible surface,
    iv) generate an isotherm for the 3D model of the ice ball at a selected temperature identified for effective ablation, and
    v) generate on the display a user interface showing the 3D model of the ice ball and the isotherm.

18. The system of claim 17, further wherein the computer system contains a model of the targeted tissue registered to the patient, still further wherein the user interface shows a representation of the targeted tissue relative to the 3D model of the ice ball and the isotherm.

19. The system of claim 18, wherein the programming further causes the computer system to compare the 3D model of the ice ball against a known size and shape of the targeted tissue to identify portions of the targeted tissue outside the isotherm; and further wherein shows the identified portions of the targeted tissue using an identifiable distinguishing visual characteristic.

20. The system of claim 17, wherein the programming causes the computer system to generate the 3D model of the ice ball by causing the computer system to:
  i) identify an axis for the cryoprobe,
  ii) identify 3D positions on the visible surface of the ice ball,
  iii) reflect the identified 3D positions across the axis for the cryoprobe to identify points on a hidden surface of the ice ball, and
  iv) combine the 3D positions on the visible surface with the identified points on the hidden surface.

21. The system of claim 20, wherein the identified 3D positions reflect across the axis for the cryoprobe perpendicularly from the axis and the points are equidistance from the axis as the identified 3D positions.

22. The system of claim 20, wherein only a selected number of 3D positions are reflected, and the 3D model of the ice ball approximates positions between the selected number of 3D positions on the visible surface and the points on the hidden surface.

23. The system of claim 17, wherein generating the isotherm for the 3D model at the selected temperature comprises:
  i) identifying a known distance from a perimeter of the ice ball known to be at the selected temperature or colder;
  ii) identifying the isotherm that is at that known distance from the perimeter of the ice ball.

24. The system of claim 23, wherein in the known distance is determined through testing of temperatures in cryoablation tests.

25. The system of claim 23, further comprising requiring that the selected temperature or colder be sustained for a determined time period.

26. The system of claim 25, wherein the determined time period is at least three minutes.

27. A computer system in communication with a cryoprobe, ultrasound device, and a display, the computer system comprising:
  a) a processor; and
  b) programming causing the processor to:
    i) receive 2D image slices of targeted tissue in a patient from the ultrasound device as it rotates within the patient, the 2D image slices containing representations of an ice ball as being formed by the cryoprobe,
    ii) combine the 2D image slices to identify a visible surface of the ice ball,
    iii) generate a 3D model of the ice ball based on the visible surface,
    iv) generate an isotherm for the 3D model of the ice ball at a selected temperature identified for effective ablation, and
    v) generate on the display a user interface showing the 3D model of the ice ball and the isotherm.

* * * * *